United States Patent [19]
Mueller et al.

[11] Patent Number: 5,196,423
[45] Date of Patent: Mar. 23, 1993

[54] UNSATURATED CYCLOHEXYLACETIC ACID DERIVATIVES, AND CROP-PROTECTION AGENTS CONTAINING SAME

[75] Inventors: Bernd Mueller, Frankenthal; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 899,158

[22] Filed: Jun. 15, 1992

Related U.S. Application Data

[63] Continuation of Ser. No. 641,900, Jan. 16, 1991, abandoned.

[30] Foreign Application Priority Data

Jan. 20, 1990 [DE] Fed. Rep. of Germany ....... 4001618

[51] Int. Cl.$^5$ ................. C07C 321/22; C07D 241/02; C07D 215/16; C07D 333/32
[52] U.S. Cl. ...................................... 514/255; 549/65; 549/66; 558/414; 558/430; 558/436; 560/9; 560/17; 560/125; 562/431; 562/507
[58] Field of Search ....... 560/9, 17, 125; 562/431, 507; 514/255, 256, 269, 311, 345, 351, 367, 374, 394, 412, 443, 529, 532, 534, 538, 543, 521, 527; 544/410, 316, 318; 546/178, 348; 548/165, 179, 217, 221, 243, 247; 549/65, 66; 558/414, 430, 436

[56] References Cited

U.S. PATENT DOCUMENTS 4,299,969 11/1981 Huffman et al. ................... 560/9
4,822,908 4/1989 Karbach et al. ................... 560/60

Primary Examiner—Jos ACu/e/ G. Dees
Assistant Examiner—Vera C. Clarke
Attorney, Agent, or Firm—Oblon, Spivak, McClelland, Maier & Neustadt

[57] ABSTRACT

Unsaturated cyclohexylacetic acid derivatives of the formula I

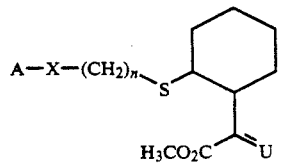

where
U is =NOCH$_3$, =CHOCH$_3$, =CH$_2$, =CH—CH$_3$, =CH—CH$_2$—CH$_3$, =N—NH—CH$_3$ or =CH—S—CH$_3$,
n is from 0 to 10,
A is hydrogen or substituted or unsubstituted alkyl, cycloalkyl, aryl or hetaryl, and
X is a single bond when n is 0, and oxygen, sulfur or a single bond when n is not 0, and the plant-compatible acid addition products and base addition products thereof, and fungicides and insecticides containing these compounds.

5 Claims, No Drawings

UNSATURATED CYCLOHEXYLACETIC ACID DERIVATIVES, AND CROP-PROTECTION AGENTS CONTAINING SAME

This application is a continuation of application Ser. No. 07/641,900, filed on Jan. 16, 1991, now abandoned.

The present invention relates to cyclohexylacetic acid derivatives having a fungicidal and insecticidal action, to fungicides and insecticides containing these compounds, and to a method of combating fungi.

We have found that unsaturated cyclohexylacetic acid derivatives of the formula I

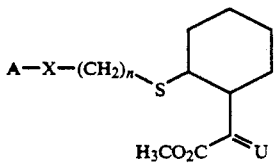

I where
U is =NOCH$_3$, =CHOCH$_3$, =CH$_2$=CH—CH$_3$, =CH—CH$_2$—CH$_3$, =N—NH—CH$_3$ or =CH—S—CH$_3$,
n is from 0 to 10,
A is hydrogen or substituted or unsubstituted alkyl, cycloalkyl, aryl or hetaryl, and
X is a single bond in the case where n=0, and oxygen, sulfur or a single bond in the case where n is not 0, and the plant-compatible acid-addition products and base-addition products thereof have a high fungitoxic and insecticidal action and very good plant compatibility.

Examples of acids for acid-addition products are mineral acids, e.g. hydrochloric acid, hydrobromic acid, phosphoric acid, sulfuric acid or nitric acid, or carboxylic acids, such as formic acid, acetic acid, oxalic acid, malonic acid, lactic acid, malic acid, succinic acid, tartaric acid, citric acid or salicylic acid, p-toluenesulfonic acid, dodecylbenzenesulfonic acid, or proton-acidic compounds in general, e.g. saccharin.

Examples of bases for base-addition products are potassium hydroxide, potassium carbonate, sodium hydroxide, sodium carbonate and ammonium hydroxide.

The novel compounds of the formula I may be produced as mixtures of stereoisomers (E/Z isomers, diastereomers or enantiomers), which can be resolved into the individual components in a conventional manner, for example by crystallization or chromatography. The individual isomers and their mixtures can be used as fungicides or insecticides and are included in the invention.

If U can occur in syn/anti-isomers, the invention relates to all the isomers, in particular the anti-isomers.

In particular, the invention relates to all the diastereomers, in particular those having a bis-equatorial arrangement at the two centers of chirality in the cyclohexane ring.

U is =NOCH$_3$, =CHOCH$_3$, =CH$_2$, =CH—CH$_3$, =CH—CH$_2$—CH$_3$, =N—NH—CH$_3$ or =CH—S—CH$_3$, in particular =O, =NOCH$_3$, =CH—OCH$_3$ or =CH—CH$_3$, preferably =NOCH$_3$.

n is from 0 to 10, in particular from 0 to 5, preferably 0, 1, 2 or 3.

A is, for example, a saturated or unsaturated, straight-chain or branched hydrocarbon radical having from 1 to 6, in particular from 1 to 4, carbon atoms or a C$_3$–C$_6$-cycloalkyl radical, or phenyl, thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl, or quinoxalyl, the cycloalkyls, alkyls, aryls or hetaryls mentioned being unsubstituted or substituted by from 1 to 3 identical or different substituents from the group comprising halogen, eg. fluorine, chlorine, bromine or iodine, C$_1$–C$_8$-alkyl, C$_1$–C$_8$-alkylthio, C$_1$–C$_8$-alkylsulfinyl, cyano, hydroxyl, nitro, C$_1$–C$_8$-alkoximino, C$_1$–C$_8$-alkoxy, phenyl, C$_1$–C$_4$-haloalkyl, C$_1$–C$_8$-alkenyloximino, formyl, C$_1$–C$_9$-alkylcarbonyl or C$_1$–C$_8$-alkoxycarbonyl, or phenyl which is substituted by from 1 to 3 identical or different substituents from the group comprising halogen, e.g. fluorine, chlorine, bromine or iodine, C$_1$–C$_8$-alkyl, C$_1$–C$_8$-alkylthio, C$_1$–C$_8$-alkylsulfinyl, cyano, hydroxyl, nitro, C$_1$–C$_8$-alkoximino, C$_1$–C$_8$-alkoxy, phenyl, C$_1$–C$_4$-haloalkyl, C$_1$–C$_8$-alkenyloximino, formyl or C$_1$–C$_9$-alkylcarbonyl.

A is preferably a saturated or unsaturated, straight-chain or branched hydrocarbon radical having from 1 to 6, in particular from 1 to 4, carbon atoms or a C$_3$–C$_6$-cycloalkyl radical, or phenyl, pyridyl or benzimidazolyl.

The novel compounds can be prepared, for example, by the following processes:

Methyl α-cyclohexen-1-yl-α-oxoacetate 1 (G. Neef et al., THL 1977 (32), 2825–8) is reacted with a thiol 2, if necessary with base catalysis, to give a thioether 3 (Y. Vankar et al., J. Chem. Research 1989, 178–179) (scheme 1).

Scheme 1

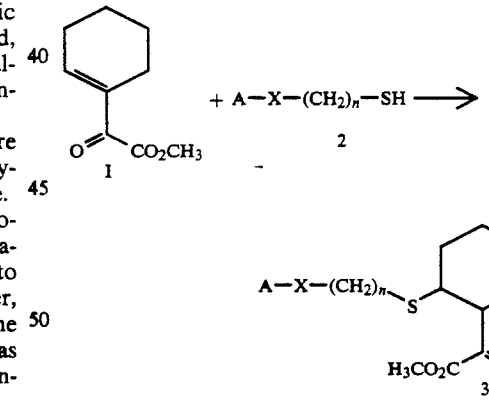

A and n are as above.

Substituted methyl α-oxoacetates 3 are converted into the active ingredients 4 by reaction with CH$_3$—O—NH$_3$Cl or H$_2$N—NH—CH$_3$ (scheme 2).

Scheme 2

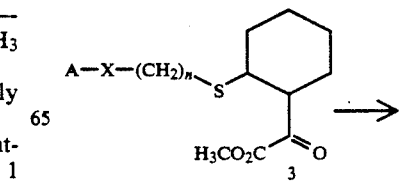

-continued

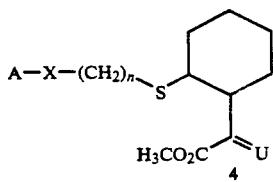

U is =NOCH$_3$ or =N—NHCH$_3$, and A and n are as above.

The methyl α-octoacetates 3 can be used to prepare the compounds 5 by a Witting reaction with (C$_6$H$_5$)$_3$P$^+$—CH$_3$X$^-$, (C$_6$H$_5$)$_3$P$^+$—CH$_2$—CH$_3$X$^-$, (C$_6$H$_5$)$_3$P$^+$—CH$_2$—CH$_2$—CH$_3$X$^-$ (X=halogen) or (C$_6$H$_5$)$_3$P$^+$—CH$_2$—O—CH$_3$Cl$^-$, (C$_6$H$_5$)$_2$P(=O)—CH$_2$—O—CH$_3$ or by Peterson olefin formation using (CH$_3$)$_3$Si—CH$_2$—O—CH$_3$ (scheme 3).

Scheme 3

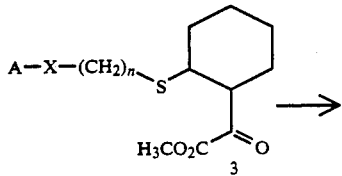

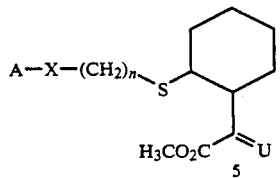

U is =CH$_2$, =CH—CH$_3$, =CH—CH$_2$—CH$_3$ or =CHOCH$_3$, and A and n are as above.

The thioenol ethers 7 can be obtained from the enol ethers 6 by reaction with methyl mercaptan (EP 178 826; scheme 4).

Scheme 4

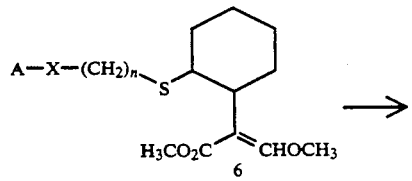

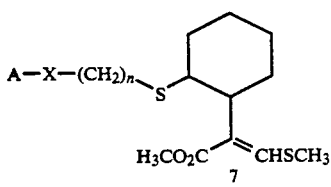

A and n are as above.

The examples below illustrate the preparation of novel compounds.

EXAMPLE 1

Methyl α-(2-benzylthiocyclohexyl)-α-oxoacetate (Compound No. 1.15)

2 g (12 mmol) of methyl α-cyclohexenyl-α-oxoacetate, 1.5 g (12 mmol) of benzyl mercaptan and 1 g (10 mmol) of triethylamine in 10 ml of methylene chloride are stirred at room temperature (20° C.) for 15 hours.

After the stirring period, water is added to the batch, and the aqueous phase is extracted with methylene chloride. The organic phase is extracted with water, dried over MgSO$_4$ and evaporated.

Chromatographic purification of the crude product gives 2.3 g (66%) of the title compound as a pale yellow oil.

IR (cm$^{-1}$): 2933, 1727, 1277, 1069.

EXAMPLE 2

Methyl α-(2-benzylthiocyclohexyl)-α-oxoacetate O-methyl oxime (Compound No. 2.15)

2.3 g (7.9 mmol) of methyl α-(2-benzylthiocyclohexyl)-α-oxoacetate (Example 1) and 0.66 g (8 mmol) of methoxyamine hydrochloride in 15 ml of methanol are stirred at room temperature for 15 hours.

Water is added to the reaction mixture, and the aqueous phase is extracted with ether. The organic phase is washed with water, dried over MgSO$_4$ and evaporated. Chromatographic purification of the crude product gives 1 g (40%) of the title compound as a pale yellow oil.

IR (cm$^{-1}$): 2935, 1726, 1151, 1042.

TABLE 1

| No. | A—X—(CH$_2$)$_n$ | mp. | IR: ν(cm$^{-1}$) |
|---|---|---|---|
| 1.1 | H | | |
| 1.2 | methyl | | |
| 1.3 | ethyl | | |
| 1.4 | isopropyl | | |
| 1.5 | butyl | | |
| 1.6 | sec.-butyl | | |
| 1.7 | t-butyl | | |
| 1.8 | isobutyl | | |
| 1.9 | pentyl | | |
| 1.10 | pivaloyl | | |
| 1.11 | hexyl | | |
| 1.12 | octyl | | |
| 1.13 | decyl | | |
| 1.14 | phenyl | oil | 2935, 1729, 1276, 1069 |
| 1.15 | benzyl | oil | 2933, 1727, 1277, 1069 |
| 1.16 | phenylethyl | | |
| 1.17 | phenylpropyl | | |
| 1.18 | phenylpentyl | | |
| 1.19 | 1-naphthyl | | |
| 1.20 | 2-naphthyl | | |
| 1.21 | 2-bromophenyl | | |
| 1.22 | 3-bromophenyl | | |
| 1.23 | 4-bromophenyl | | |
| 1.24 | 2-chlorophenyl | | |
| 1.25 | 3-chlorophenyl | | |
| 1.26 | 4-chlorophenyl | | |
| 1.27 | 2-fluorophenyl | | |
| 1.28 | 3-fluorophenyl | | |
| 1.29 | 4-fluorophenyl | | |
| 1.30 | 2-methylphenyl | | |
| 1.31 | 3-methylphenyl | | |
| 1.32 | 4-methylphenyl | | |
| 1.33 | 2-ethyl-phenyl | | |
| 1.34 | 3-ethyl-phenyl | | |
| 1.35 | 4-ethyl-phenyl | | |
| 1.36 | 2-iso-propyl-phenyl | | |

TABLE 1-continued

A—X—(CH₂)ₙ—S—[cyclohexyl]—C(=O)—CO₂CH₃ (H₃CO₂C)

| No. | A—X—(CH₂)ₙ | mp. | IR: v(cm⁻¹) |
|---|---|---|---|
| 1.37 | 3-iso-propyl-phenyl | | |
| 1.38 | 4-iso-propyl-phenyl | | |
| 1.39 | 2-tert.-butyl-phenyl | | |
| 1.40 | 3-tert.-butyl-phenyl | | |
| 1.41 | 4-tert.-butyl-phenyl | | |
| 1.42 | 4-butyl-phenyl | | |
| 1.43 | 4-hexyl-phenyl | | |
| 1.44 | 4-nonyl-phenyl | | |
| 1.45 | 4-decyl-phenyl | | |
| 1.46 | 2-methoxy-phenyl | | |
| 1.47 | 3-methoxy-phenyl | | |
| 1.48 | 4-methoxy-phenyl | | |
| 1.49 | 2-trifluoromethyl-phenyl | | |
| 1.50 | 3-trifluoromethyl-phenyl | | |
| 1.51 | 4-trifluoromethyl-phenyl | | |
| 1.52 | 2-formylphenyl | | |
| 1.53 | 3-formylphenyl | | |
| 1.54 | 4-formylphenyl | | |
| 1.55 | 2-allyl-O—N=CH-phenyl | | |
| 1.56 | 3-allyl-O—N=CH-phenyl | | |
| 1.57 | 4-allyl-O—N—CH-phenyl | | |
| 1.58 | 2-nitro-phenyl | | |
| 1.59 | 3-nitro-phenyl | | |
| 1.60 | 2,4-dichlorophenyl | | |
| 1.61 | 2,5-dichlorophenyl | | |
| 1.62 | 2,6-dichlorophenyl | | |
| 1.63 | 3,4-dichlorophenyl | | |
| 1.64 | 2,3-dichlorophenyl | | |
| 1.65 | 3,5-dichlorophenyl | | |
| 1.66 | 2,3,4-trichlorophenyl | | |
| 1.67 | 2,4,5-trichlorophenyl | | |
| 1.68 | 2,4,6-trichlorophenyl | | |
| 1.69 | 2,3,4,6-tetrachlorophenyl | | |
| 1.70 | 2,3,4,5,6-pentachlorophenyl | | |
| 1.71 | 2,3,4,5-tetrafluorophenyl | | |
| 1.72 | 2,3,5,6-tetrafluorophenyl | | |
| 1.73 | 2,3,4,5,6-pentafluorophenyl | | |
| 1.74 | 2-chloro, 4-fluorophenyl | | |
| 1.75 | 3-chloro, 4-fluorophenyl | | |
| 1.76 | 2-chloro, 6-methyl-phenyl | | |
| 1.77 | 4-chloro, 2-methyl-phenyl | | |
| 1.78 | 2,4-dichloro, 5-methyl-phenyl | | |
| 1.79 | 4-chloro, 2,5-dimethyl-phenyl | | |
| 1.80 | 4-bromo, 2-methyl-phenyl | | |
| 1.81 | 3,5-bistrifluoromethyl-phenyl | | |
| 1.82 | 2,3-dimethyl-phenyl | | |
| 1.83 | 2,4-dimethyl-phenyl | | |
| 1.84 | 2,5-dimethyl-phenyl | | |
| 1.85 | 2,6-dimethyl-phenyl | | |
| 1.86 | 3,4-dimethyl-phenyl | | |
| 1.87 | 3,5-dimethyl-phenyl | | |
| 1.88 | 2,4,5-trimethyl-phenyl | | |
| 1.89 | 2,6-diethyl-phenyl | | |
| 1.90 | 2,4-di-tert.-butyl-phenyl | | |
| 1.91 | 2,5-dimethoxy-phenyl | | |
| 1.92 | 3,4-dimethoxy-phenyl | | |
| 1.93 | 2-methyl, 4-tert.-butyl-phenyl | | |
| 1.94 | 2-methoxycarbonyl-phenyl | | |
| 1.95 | 2-ethoxycarbonyl-phenyl | | |
| 1.96 | 2-propoxycarbonyl-phenyl | | |
| 1.97 | 2-butoxycarbonyl-phenyl | | |
| 1.98 | 2-cyano-phenyl | | |
| 1.99 | 3-cyano-phenyl | | |
| 1.100 | 4-cyano-phenyl | | |
| 1.101 | 1-naphthylmethyl | | |
| 1.102 | 2-naphthylmethyl | | |
| 1.103 | 2-bromobenzyl | | |
| 1.104 | 3-bromobenzyl | | |
| 1.105 | 4-bromobenzyl | | |
| 1.106 | 2-chlorobenzyl | | |
| 1.107 | 3-chlorobenzyl | | |
| 1.108 | 4-chlorobenzyl | | |
| 1.109 | 2-fluorobenzyl | | |
| 1.110 | 3-fluorobenzyl | | |
| 1.111 | 4-fluorobenzyl | | |
| 1.112 | 2-methylbenzyl | | |
| 1.113 | 3-methylbenzyl | | |
| 1.114 | 4-methylbenzyl | | |
| 1.115 | 2-methoxybenzyl | | |
| 1.116 | 3-methoxybenzyl | | |
| 1.117 | 4-methoxybenzyl | | |
| 1.118 | 4-ethoxybenzyl | | |
| 1.119 | 4-butyloxybenzyl | | |
| 1.120 | 4-benzyloxybenzyl | | |
| 1.121 | 2-trifluoromethyl-benzyl | | |
| 1.122 | 3-trifluoromethyl-benzyl | | |
| 1.123 | 4-trifluoromethyl-benzyl | | |
| 1.124 | 2-formylbenzyl | | |
| 1.125 | 3-formylbenzyl | | |
| 1.126 | 4-formylbenzyl | | |
| 1.127 | 2-allyl-O—N=CH-benzyl | | |
| 1.128 | 3-allyl-O—N=CH-benzyl | | |
| 1.129 | 4-allyl-O—N=CH-benzyl | | |
| 1.130 | 2-nitrobenzyl | | |
| 1.131 | 3-nitrobenzyl | | |
| 1.132 | 2,4-dichlorobenzyl | | |
| 1.133 | 2,6-dichlorobenzyl | | |
| 1.134 | 3,4-dichlorobenzyl | | |
| 1.135 | 2,3-dichlorobenzyl | | |
| 1.136 | 3,5-dichlorobenzyl | | |
| 1.137 | 2,3-dimethylbenzyl | | |
| 1.138 | 2,4-dimethylbenzyl | | |
| 1.139 | 2,5-dimethylbenzyl | | |
| 1.140 | 2,6-dimethylbenzyl | | |
| 1.141 | 3,4-dimethylbenzyl | | |
| 1.142 | 3,5-dimethylbenzyl | | |
| 1.143 | 4-chloro-2-methylbenzyl | | |
| 1.144 | 2-methoxycarbonyl-benzyl | | |
| 1.145 | 2-ethoxycarbonyl-benzyl | | |
| 1.146 | 2-butoxycarbonyl-benzyl | | |
| 1.147 | 2-cyano-benzyl | | |
| 1.148 | 3-cyano-benzyl | | |
| 1.149 | 4-cyano-benzyl | | |
| 1.150 | 2-pyridyl | | |
| 1.151 | 3-pyridyl | | |
| 1.152 | 4-pyridyl | | |
| 1.153 | 6-methyl-2-pyridyl | | |
| 1.154 | 6-ethyl-2-pyridyl | | |
| 1.155 | 6-n-propyl-2-pyridyl | | |
| 1.156 | 6-n-butyl-2-pyridyl | | |
| 1.157 | 6-tert.-butyl-2-pyridyl | | |
| 1.158 | 6-n-hexyl-2-pyridyl | | |
| 1.159 | 6-phenyl-2-pyridyl | | |
| 1.160 | 6-benzyl-2-pyridyl | | |
| 1.161 | 6-trifluoromethyl-2-pyridyl | | |
| 1.162 | 6-methoxy-2-pyridyl | | |
| 1.163 | 6-chloro-2-pyridyl | | |
| 1.164 | 3,6-dimethyl-2-pyridyl | | |
| 1.165 | 4,6-dimethyl-2-pyridyl | | |
| 1.166 | 5,6-dimethyl-2-pyridyl | | |
| 1.167 | 4-phenyl-6-methyl-2-pyridyl | | |
| 1.168 | 3,4-dichloro-6-methyl-2-pyridyl | | |
| 1.169 | 3,4,5-trichloro-6-methyl-2-pyridyl | | |
| 1.170 | 4-trifluoromethyl-6-methyl-2-pyridyl | | |
| 1.171 | 3-acetyl-4,6-dimethyl-2-pyridyl | | |
| 1.172 | 3-cyano-6-methyl-2-pyridyl | | |
| 1.173 | 3-cyano-6-phenyl-2-pyridyl | | |
| 1.174 | 3-methyloxycarbonyl-2-pyridyl | | |
| 1.175 | 3-methyloxycarbonyl-6-iso-propyl-2-pyridyl | | |
| 1.176 | 5-trifluoromethyl-2-pyridyl | | |
| 1.177 | 2-quinolyl | | |
| 1.178 | 3-methyl-2-quinolyl | | |
| 1.179 | 4-phenyl-2-quinolyl | | |

TABLE 1-continued

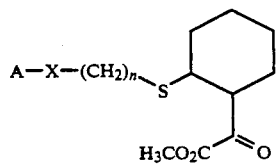

| No. | A—X—(CH$_2$)$_n$ | mp. | IR: v(cm$^{-1}$) |
|---|---|---|---|
| 1.180 | 8-chloro-2-quinolyl | | |
| 1.181 | 4-methyl-8-methoxy-2-quinolyl | | |
| 1.182 | 4-quinolyl | | |
| 1.183 | 2,6-dimethyl-4-quinolyl | | |
| 1.184 | 8-quinolyl | | |
| 1.185 | 5,7-dichloro-8-quinolyl | | |
| 1.186 | 2-pyrimidinyl | | |
| 1.187 | 4-trifluoromethyl-2-pyrimidinyl | | |
| 1.188 | 4,6-dimethyl-5-chloro-2-pyrimidinyl | | |
| 1.189 | 3,5-dimethyl-4-pyrimidinyl | | |
| 1.190 | 2-pyrazinyl | | |
| 1.191 | 2-thienyl | | |
| 1.192 | 3-thienyl | | |
| 1.193 | 3-methyl-2-quinoxalinyl | | |
| 1.194 | 3-phenyl-5-isoxazolyl | | |
| 1.195 | 2-benzoxazolyl | | |
| 1.196 | 2-benzthiazolyl | | |
| 1.197 | 4-chloro-2-benzothiazolyl | | |
| 1.198 | 5-chloro-2-benzothiazolyl | | |
| 1.199 | 6-chloro-2-benzothiazolyl | | |
| 1.200 | 6-methyl-2-benzothiazolyl | | |
| 1.201 | 6-methoxy-2-benzothiazolyl | | |

TABLE 2

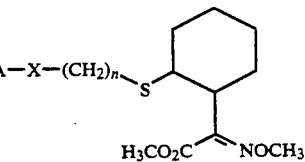

| No. | A—X—(CH$_2$)$_n$ | mp. | IR: v(cm$^{-1}$) |
|---|---|---|---|
| 2.1 | H | | |
| 2.2 | methyl | | |
| 2.3 | ethyl | | |
| 2.4 | isopropyl | | |
| 2.5 | butyl | | |
| 2.6 | sec.-butyl | | |
| 2.7 | t-butyl | | |
| 2.8 | isobutyl | | |
| 2.9 | pentyl | | |
| 2.10 | pivaloyl | | |
| 2.11 | hexyl | | |
| 2.12 | octyl | | |
| 2.13 | decyl | | |
| 2.14 | phenyl | oil | 2935, 1738, 1722, 1152, 1043 |
| 2.15 | benzyl | oil | 2935, 1726, 1151, 1042 |
| 2.16 | phenylethyl | | |
| 2.17 | phenylpropyl | | |
| 2.18 | phenylpentyl | | |
| 2.19 | 1-naphthyl | | |
| 2.20 | 2-naphthyl | | |
| 2.21 | 2-bromophenyl | | |
| 2.22 | 3-bromophenyl | | |
| 2.23 | 4-bromophenyl | | |
| 2.24 | 2-chlorophenyl | | |
| 2.25 | 3-chlorophenyl | | |
| 2.26 | 4-chlorophenyl | | |
| 2.27 | 2-fluorophenyl | | |
| 2.28 | 3-fluorophenyl | | |
| 2.29 | 4-fluorophenyl | | |
| 2.30 | 2-methylphenyl | | |
| 2.31 | 3-methylphenyl | | |
| 2.32 | 4-methylphenyl | | |
| 2.33 | 2-ethyl-phenyl | | |
| 2.34 | 3-ethyl-phenyl | | |
| 2.35 | 4-ethyl-phenyl | | |
| 2.36 | 2-isopropyl-phenyl | | |
| 2.37 | 3-iso-propyl-phenyl | | |
| 2.38 | 4-iso-propyl-phenyl | | |
| 2.39 | 2-tert.-butyl-phenyl | | |
| 2.40 | 3-tert.-butyl-phenyl | | |
| 2.41 | 4-tert.-butyl-phenyl | | |
| 2.42 | 4-butyl-phenyl | | |
| 2.43 | 4-hexyl-phenyl | | |
| 2.44 | 4-nonyl-phenyl | | |
| 2.45 | 4-decyl-phenyl | | |
| 2.46 | 2-methoxy-phenyl | | |
| 2.47 | 3-methoxy-phenyl | | |
| 2.48 | 4-methoxy-phenyl | | |
| 2.49 | 2-trifluoromethyl-phenyl | | |
| 2.50 | 3-trifluoromethyl-phenyl | | |
| 2.51 | 4-trifluoromethyl-phenyl | | |
| 2.52 | 2-formylphenyl | | |
| 2.53 | 3-formylphenyl | | |
| 2.54 | 4-formylphenyl | | |
| 2.55 | 2-allyl-O—N=CH-phenyl | | |
| 2.56 | 3-allyl-O—N=CH-phenyl | | |
| 2.57 | 4-allyl-O—N=CH-phenyl | | |
| 2.58 | 2-nitro-phenyl | | |
| 2.59 | 3-nitro-phenyl | | |
| 2.60 | 2,4-dichlorophenyl | | |
| 2.61 | 2,5-dichlorophenyl | | |
| 2.62 | 2,6-dichlorophenyl | | |
| 2.63 | 3,4-dichlorophenyl | | |
| 2.64 | 2,3-dichlorophenyl | | |
| 2.65 | 3,5-dichlorophenyl | | |
| 2.66 | 2,3,4-trichlorophenyl | | |
| 2.67 | 2,4,5-trichlorophenyl | | |
| 2.68 | 2,4,6-trichlorophenyl | | |
| 2.69 | 2,3,4,6-tetrachlorophenyl | | |
| 2.70 | 2,3,4,5,6-pentachlorophenyl | | |
| 2.71 | 2,3,4,5-tetrafluorophenyl | | |
| 2.72 | 2,3,5,6-tetrafluorophenyl | | |
| 2.73 | 2,3,4,5,6-pentafluorophenyl | | |
| 2.74 | 2-chloro, 4-fluorophenyl | | |
| 2.75 | 3-chloro, 4-fluorophenyl | | |
| 2.76 | 2-chloro, 6-methyl-phenyl | | |
| 2.77 | 4-chloro, 2-methyl-phenyl | | |
| 2.78 | 2,4-dichloro, 5-methyl-phenyl | | |
| 2.79 | 4-chloro, 2,5-dimethyl-phenyl | | |
| 2.80 | 4-bromo, 2-methyl-phenyl | | |
| 2.81 | 3,5-bistrifluoromethyl-phenyl | | |
| 2.82 | 2,3-dimethyl-phenyl | | |
| 2.83 | 2,4-dimethyl-phenyl | | |
| 2.84 | 2,5-dimethyl-phenyl | | |
| 2.85 | 2,6-dimethyl-phenyl | | |
| 2.86 | 3,4-dimethyl-phenyl | | |
| 2.87 | 3,5-dimethyl-phenyl | | |
| 2.88 | 2,4,5-trimethyl-phenyl | | |
| 2.89 | 2,6-diethyl-phenyl | | |
| 2.90 | 2,4-di-tert.-butyl-phenyl | | |
| 2.91 | 2,5-dimethoxy-phenyl | | |
| 2.92 | 3,4-dimethoxy-phenyl | | |
| 2.93 | 2-methyl, 4-tert.-butyl-phenyl | | |
| 2.94 | 2-methoxycarbonyl-phenyl | | |
| 2.95 | 2-ethoxycarbonyl-phenyl | | |
| 2.96 | 2-propoxycarbonyl-phenyl | | |
| 2.97 | 2-butoxycarbonyl-phenyl | | |
| 2.98 | 2-cyano-phenyl | | |
| 2.99 | 3-cyano-phenyl | | |
| 2.100 | 4-cyano-phenyl | | |
| 2.101 | 1-naphthylmethyl | | |
| 2.102 | 2-naphthylmethyl | | |
| 2.103 | 2-bromobenzyl | | |
| 2.104 | 3-bromobenzyl | | |
| 2.105 | 4-bromobenzyl | | |

TABLE 2-continued

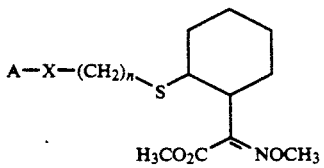

| No. | A—X—(CH$_2$)$_n$ | mp. | IR: ν(cm$^{-1}$) |
|---|---|---|---|
| 2.106 | 2-chlorobenzyl | | |
| 2.107 | 3-chlorobenzyl | | |
| 2.108 | 4-chlorobenzyl | | |
| 2.109 | 2-fluorobenzyl | | |
| 2.110 | 3-fluorobenzyl | | |
| 2.111 | 4-fluorobenzyl | | |
| 2.112 | 2-methylbenzyl | | |
| 2.113 | 3-methylbenzyl | | |
| 2.114 | 4-methylbenzyl | | |
| 2.115 | 2-methoxybenzyl | | |
| 2.116 | 3-methoxybenzyl | | |
| 2.117 | 4-methoxybenzyl | | |
| 2.118 | 4-ethoxybenzyl | | |
| 2.119 | 4-butyloxybenzyl | | |
| 2.120 | 4-benzyloxybenzyl | | |
| 2.121 | 2-trifluoromethyl-benzyl | | |
| 2.122 | 3-trifluoromethyl-benzyl | | |
| 2.123 | 4-trifluoromethyl-benzyl | | |
| 2.124 | 2-formylbenzyl | | |
| 2.125 | 3-formylbenzyl | | |
| 2.126 | 4-formylbenzyl | | |
| 2.127 | 2-allyl-O—N=CH-benzyl | | |
| 2.128 | 3-allyl-O—N=CH-benzyl | | |
| 2.129 | 4-allyl-O—N=CH-benzyl | | |
| 2.130 | 2-nitrobenzyl | | |
| 2.131 | 3-nitrobenzyl | | |
| 2.132 | 2,4-dichlorobenzyl | | |
| 2.133 | 2,6-dichlorobenzyl | | |
| 2.134 | 3,4-dichlorobenzyl | | |
| 2.135 | 2,3-dichlorobenzyl | | |
| 2.136 | 3,5-dichlorobenzyl | | |
| 2.137 | 2,3-dimethylbenzyl | | |
| 2.138 | 2,4-dimethylbenzyl | | |
| 2.139 | 2,5-dimethylbenzyl | | |
| 2.140 | 2,6-dimethylbenzyl | | |
| 2.141 | 3,4-dimethylbenzyl | | |
| 2.142 | 3,5-dimethylbenzyl | | |
| 2.143 | 4-chloro-2-methylbenzyl | | |
| 2.144 | 2-methoxycarbonyl-benzyl | | |
| 2.145 | 2-ethoxycarbonyl-benzyl | | |
| 2.146 | 2-butoxycarbonyl-benzyl | | |
| 2.147 | 2-cyano-benzyl | | |
| 2.148 | 3-cyano-benzyl | | |
| 2.149 | 4-cyano-benzyl | | |
| 2.150 | 2-pyridyl | | |
| 2.151 | 3-pyridyl | | |
| 2.152 | 4-pyridyl | | |
| 2.153 | 6-methyl-2-pyridyl | | |
| 2.154 | 6-ethyl-2-pyridyl | | |
| 2.155 | 6-n-propyl-2-pyridyl | | |
| 2.156 | 6-n-butyl-2-pyridyl | | |
| 2.157 | 6-tert.-butyl-2-pyridyl | | |
| 2.158 | 6-n-hexyl-2-pyridyl | | |
| 2.159 | 6-phenyl-2-pyridyl | | |
| 2.160 | 6-benzyl-2-pyridyl | | |
| 2.161 | 6-trifluoromethyl-2-pyridyl | | |
| 2.162 | 6-methoxy-2-pyridyl | | |
| 2.163 | 6-chloro-2-pyridyl | | |
| 2.164 | 3,6-dimethyl-2-pyridyl | | |
| 2.165 | 4,6-dimethyl-2-pyridyl | | |
| 2.166 | 5,6-dimethyl-2-pyridyl | | |
| 2.167 | 4-phenyl-6-methyl-2-pyridyl | | |
| 2.168 | 3,4-dichloro-6-methyl-2-pyridyl | | |
| 2.169 | 3,4,5-trichloro-6-methyl-2-pyridyl | | |
| 2.170 | 4-trifluoromethyl-6-methyl-2-pyridyl | | |
| 2.171 | 3-acetyl-4,6-dimethyl-2-pyridyl | | |
| 2.172 | 3-cyano-6-methyl-2-pyridyl | | |
| 2.173 | 3-cyano-6-phenyl-2-pyridyl | | |
| 2.174 | 3-methyloxycarbonyl-2-pyridyl | | |
| 2.175 | 3-methyloxycarbonyl-6-isopropyl-2-pyridyl | | |

TABLE 2-continued

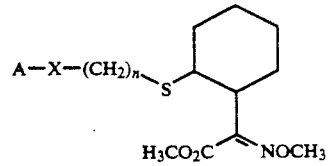

| No. | A—X—(CH$_2$)$_n$ | mp. | IR: ν(cm$^{-1}$) |
|---|---|---|---|
| 2.176 | 5-trifluoromethyl-2-pyridyl | | |
| 2.177 | 2-quinolyl | | |
| 2.178 | 3-methyl-2-quinolyl | | |
| 2.179 | 4-phenyl-2-quinolyl | | |
| 2.180 | 8-chloro-2-quinolyl | | |
| 2.181 | 4-methyl-8-methoxy-2-quinolyl | | |
| 2.182 | 4-quinolyl | | |
| 2.183 | 2,6-dimethyl-4-quinolyl | | |
| 2.184 | 8-quinolyl | | |
| 2.185 | 5,7-dichloro-8-quinolyl | | |
| 2.186 | 2-pyrimidinyl | | |
| 2.187 | 4-trifluoromethyl-2-pyrimidinyl | | |
| 2.188 | 4,6-dimethyl-5-chloro-2-pyrimidinyl | | |
| 2.189 | 3,5-dimethyl-4-pyrimidinyl | | |
| 2.190 | 2-pyrazinyl | | |
| 2.191 | 2-thienyl | | |
| 2.192 | 3-thienyl | | |
| 2.193 | 3-methyl-2-quinoxalinyl | | |
| 2.194 | 3-phenyl-5-isoxazolyl | | |
| 2.195 | 2-benzoxazolyl | | |
| 2.196 | 2-benzthiazolyl | | |
| 2.197 | 4-chloro-2-benzothiazolyl | | |
| 2.198 | 5-chloro-2-benzothiazolyl | | |
| 2.199 | 6-chloro-2-benzothiazolyl | | |
| 2.200 | 6-methyl-2-benzothiazolyl | | |
| 2.201 | 6-methoxy-2-benzothiazolyl | | |

TABLE 3

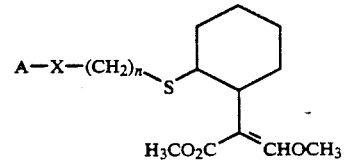

| No. | A—X—(CH$_2$)$_n$ | mp. | IR: ν(cm$^{-1}$) |
|---|---|---|---|
| 3.1 | n-butyl | | |
| 3.2 | phenyl | | |
| 3.3 | 2-methoxyphenyl | | |
| 3.4 | 3-methoxyphenyl | | |
| 3.5 | 4-methoxyphenyl | | |
| 3.6 | 2-chlorophenyl | | |
| 3.7 | 3-chlorophenyl | | |
| 3.8 | 4-chlorophenyl | | |
| 3.9 | 2-methylphenyl | | |
| 3.10 | 3-methylphenyl | | |
| 3.11 | 4-methylphenyl | | |
| 3.12 | 2,3-dimethylphenyl | | |
| 3.13 | 2,4-dimethylphenyl | | |
| 3.14 | 2,5-dimethylphenyl | | |
| 3.15 | 2,6-dimethylphenyl | | |
| 3.16 | 3,4-dimethylphenyl | | |
| 3.17 | 3,5-dimethylphenyl | | |
| 3.18 | 4-chloro-2-methylphenyl | | |
| 3.19 | 4-methoxycarbonylphenyl | | |
| 3.20 | 4-ethoxycarbonylphenyl | | |
| 3.21 | 4-butoxycarbonylphenyl | | |
| 3.22 | 2-allyl-O—N=CH-phenyl | | |
| 3.23 | 3-allyl-O—N=CH-phenyl | | |
| 3.24 | 4-allyl-O—N=CH-phenyl | | |
| 3.25 | 2-pyridyl | | |
| 3.26 | 6-methyl-2-pyridyl | | |
| 3.27 | 6-chloro-2-pyridyl | | |
| 3.28 | 4-chloro-2-benzothiazolyl | | |
| 3.29 | 5-chloro-2-benzothiazolyl | | |
| 3.30 | 6-chloro-2-benzothiazolyl | | |

TABLE 3-continued

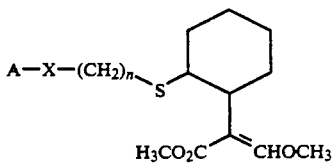

| No. | A—X—(CH$_2$)$_n$ | mp. | IR: v(cm$^{-1}$) |
|---|---|---|---|
| 3.31 | 2-methoxybenzyl | | |
| 3.32 | 3-methoxybenzyl | | |
| 3.33 | 4-methoxybenzyl | | |
| 3.34 | 2-chlorobenzene | | |
| 3.35 | 3-chlorobenzene | | |
| 3.36 | 4-chlorobenzyl | | |
| 3.37 | 2-methylbenzyl | | |
| 3.38 | 3-methylbenzyl | | |
| 3.39 | 4-methylbenzyl | | |
| 3.40 | 2,3-dimethylbenzyl | | |
| 3.41 | 2,4-dimethylbenzyl | | |
| 3.42 | 2,5-dimethylbenzyl | | |
| 3.43 | 2,6-dimethylbenzyl | | |
| 3.44 | 3,4-dimethylbenzyl | | |
| 3.45 | 3,5-dimethylbenzyl | | |
| 3.46 | 4-chloro-2-methylbenzyl | | |
| 3.47 | 4-methoxycarbonylbenzyl | | |
| 3.48 | 4-ethoxycarbonylbenzyl | | |
| 3.49 | 4-butoxycarbonylbenzyl | | |
| 3.50 | 2-allyl-O—N=CH-phenyl | | |
| 3.51 | 3-allyl-O—N=CH-phenyl | | |
| 3.52 | 4-allyl-O—N=CH-phenyl | | |

TABLE 4

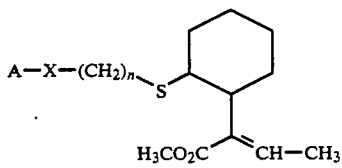

| No. | A—X—(CH$_2$)$_n$ | mp. | IR: v(cm$^{-1}$) |
|---|---|---|---|
| 4.1 | n-butyl | | |
| 4.2 | phenyl | | |
| 4.3 | 2-methoxyphenyl | | |
| 4.4 | 3-methoxyphenyl | | |
| 4.5 | 4-methoxyphenyl | | |
| 4.6 | 2-chlorophenyl | | |
| 4.7 | 3-chlorophenyl | | |
| 4.8 | 4-chlorophenyl | | |

TABLE 4-continued

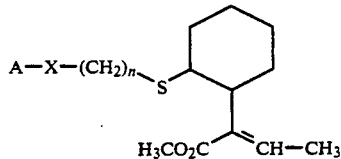

| No. | A—X—(CH$_2$)$_n$ | mp. | IR: v(cm$^{-1}$) |
|---|---|---|---|
| 4.9 | 2-methylphenyl | | |
| 4.10 | 3-methylphenyl | | |
| 4.11 | 4-methylphenyl | | |
| 4.12 | 2,3-dimethylphenyl | | |
| 4.13 | 2,4-dimethylphenyl | | |
| 4.14 | 2,5-dimethylphenyl | | |
| 4.15 | 2,6-dimethylphenyl | | |
| 4.16 | 3,4-dimethylphenyl | | |
| 4.17 | 3,5-dimethylphenyl | | |
| 4.18 | 4-chloro-2-methylphenyl | | |
| 4.19 | 4-methoxycarbonylphenyl | | |
| 4.20 | 4-ethoxycarbonylphenyl | | |
| 4.21 | 4-butoxycarbonylphenyl | | |
| 4.22 | 2-allyl-O—N=CH-phenyl | | |
| 4.23 | 3-allyl-O—N=CH-phenyl | | |
| 4.24 | 4-allyl-O—N=CH-phenyl | | |
| 4.25 | 2-pyridyl | | |
| 4.26 | 6-methyl-2-pyridyl | | |
| 4.27 | 6-chloro-2-pyridyl | | |
| 4.28 | 4-chloro-2-benzothiazolyl | | |
| 4.29 | 5-chloro-2-benzothiazolyl | | |
| 4.30 | 6-chloro-2-benzothiazolyl | | |
| 4.31 | 2-methoxybenzyl | | |
| 4.32 | 3-methoxybenzyl | | |
| 4.33 | 4-methoxybenzyl | | |
| 4.34 | 2-chlorobenzene | | |
| 4.35 | 3-chlorobenzene | | |
| 4.36 | 4-chlorobenzyl | | |
| 4.37 | 2-methylbenzyl | | |
| 4.38 | 3-methylbenzyl | | |
| 4.39 | 4-methylbenzyl | | |
| 4.40 | 2,3-dimethylbenzyl | | |
| 4.41 | 2,4-dimethylbenzyl | | |
| 4.42 | 2,5-dimethylbenzyl | | |
| 4.43 | 2,6-dimethylbenzyl | | |
| 4.44 | 3,4-dimethylbenzyl | | |
| 4.45 | 3,5-dimethylbenzyl | | |
| 4.46 | 4-chloro-2-methylbenzyl | | |
| 4.47 | 4-methoxycarbonylbenzyl | | |
| 4.48 | 4-ethoxycarbonylbenzyl | | |
| 4.49 | 4-butoxycarbonylbenzyl | | |
| 4.50 | 2-allyl-O—N=CH-phenyl | | |
| 4.51 | 3-allyl-O—N=CH-phenyl | | |
| 4.52 | 4-allyl-O—N=CH-phenyl | | |

TABLE 5

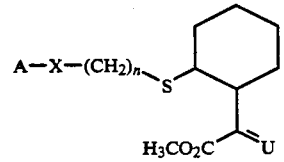

| No. | A—X—(CH$_2$)$_n$ | U | mp. | IR: v/cm$^{-1}$) |
|---|---|---|---|---|
| 5.1 | 2-methylphenyl | CH$_2$ | | |
| 5.2 | 3-methoxyphenyl | CH$_2$ | | |
| 5.3 | 4-chlorophenyl | CH$_2$ | | |
| 5.4 | 2-allyl-O—N=CH-phenyl | CH$_2$ | | |
| 5.5 | 3-methoxycarbonylphenyl | CH$_2$ | | |
| 5.6 | 6-chloro-2-pyridyl | CH$_2$ | | |
| 5.7 | 6-chloro-2-benzothiazolyl | CH$_2$ | | |
| 5.8 | 2-methylbenzyl | CH$_2$ | | |
| 5.9 | 3-methoxybenzyl | CH$_2$ | | |
| 5.10 | 4-chlorobenzyl | CH$_2$ | | |
| 5.11 | 2-allyl-O—N=CH-benzyl | CH$_2$ | | |
| 5.12 | 3-methoxycarbonyl-benzyl | CH$_2$ | | |
| 5.13 | 2-methylphenyl | CH—CH$_2$—CH$_3$ | | |

TABLE 5-continued

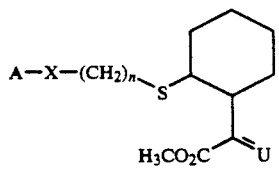

| No. | A—X—(CH$_2$)$_n$ | U | mp. | IR: v/cm$^{-1}$) |
|---|---|---|---|---|
| 5.14 | 3-methoxyphenyl | CH—CH$_2$—CH$_3$ | | |
| 5.15 | 4-chlorophenyl | CH—CH$_2$—CH$_3$ | | |
| 5.16 | 2-allyl-O—N═CH-phenyl | CH—CH$_2$—CH$_3$ | | |
| 5.17 | 3-methoxycarbonylphenyl | CH—CH$_2$—CH$_3$ | | |
| 5.18 | 6-chloro-2-pyridyl | CH—CH$_2$—CH$_3$ | | |
| 5.19 | 6-chloro-2-benzothiazolyl | CH—CH$_2$—CH$_3$ | | |
| 5.20 | 2-methylbenzyl | CH—CH$_2$—CH$_3$ | | |
| 5.21 | 3-methoxybenzyl | CH—CH$_2$—CH$_3$ | | |
| 5.22 | 4-chlorobenzyl | CH—CH$_2$—CH$_3$ | | |
| 5.23 | 2-allyl-O—N═CH-benzyl | CH—CH$_2$—CH$_3$ | | |
| 5.24 | 3-methoxycarbonyl-benzyl | CH—CH$_2$—CH$_3$ | | |
| 5.25 | 2-methylphenyl | N—NH—CH$_3$ | | |
| 5.26 | 3-methoxyphenyl | N—NH—CH$_3$ | | |
| 5.27 | 4-chlorophenyl | N—NH—CH$_3$ | | |
| 5.28 | 2-allyl-O—N═CH-phenyl | N—NH—CH$_3$ | | |
| 5.29 | 3-methoxycarbonylphenyl | N—NH—CH$_3$ | | |
| 5.30 | 6-chloro-2-pyridyl | N—NH—CH$_3$ | | |
| 5.31 | 6-chloro-2-benzothiazolyl | N—NH—CH$_3$ | | |
| 5.32 | 2-methylbenzyl | N—NH—CH$_3$ | | |
| 5.33 | 3-methoxybenzyl | N—NH—CH$_3$ | | |
| 5.34 | 4-chlorobenzyl | N—NH—CH$_3$ | | |
| 5.35 | 2-allyl-O—N═CH-benzyl | N—NH—CH$_3$ | | |
| 5.36 | 3-methoxycarbonyl-benzyl | N—NH—CH$_3$ | | |
| 5.37 | 2-methylphenyl | CH—S—CH$_3$ | | |
| 5.38 | 3-methoxyphenyl | CH—S—CH$_3$ | | |
| 5.39 | 4-chlorophenyl | CH—S—CH$_3$ | | |
| 5.40 | 2-allyl-O—N═CH-phenyl | CH—S—CH$_3$ | | |
| 5.41 | 3-methoxycarbonylphenyl | CH—S—CH$_3$ | | |
| 5.42 | 6-chloro-2-pyridyl | CH—S—CH$_3$ | | |
| 5.43 | 6-chloro-2-benzothiazolyl | CH—S—CH$_3$ | | |
| 5.44 | 2-methylbenzyl | CH—S—CH$_3$ | | |
| 5.45 | 3-methoxybenzyl | CH—S—CH$_3$ | | |
| 5.46 | 4-chlorobenzyl | CH—S—CH$_3$ | | |
| 5.47 | 2-allyl-O—N═CH-benzyl | CH—S—CH$_3$ | | |
| 5.48 | 3-methoxycarbonyl-benzyl | CH—S—CH$_3$ | | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (timber), e.g., against *Paecilomyces variotii*. When the active ingredients are used for treating seed, amounts of from 0.001 to 50, and preferably from 0.01 to 20, g per kg of seed are generally required.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 2.15 and 10 parts by weight of N-methyl-α-pyrrolidone, which is suitable for application in the form of very fine drops.

II. A mixture of 20 parts by weight of compound no. 2.15, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 2.15, 40 parts by weight of cyclohexanone, 30 parts by weight of isobutanol, 20 parts by weight of the adduct of 40 moles of ethylene oxide and 1 mole of castor oil. By pouring the solution into water and finely dispersing it therein, an aqueous dispersion is obtained.

IV. An aqueous dispersion of 20 parts by weight of compound no. 2.15, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and finely dispersing it therein, an aqueous dispersion is obtained.

V. A hammer-milled mixture of 80 parts by weight of compound no. 2.15, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 2.15 and 97 parts by weight of particulate kaolin. The dust contains 3 wt % of the active ingredient.

VII. An intimate mixture of 30 parts by weight of compound no. 2.15, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 2.15, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 2.15, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone, 2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLE

Action on Brown Rust of Wheat

Leaves of pot-grown wheat seedlings of the "Kanzler" variety were dusted with spores of brown rust (Puccinia recondita). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredient 2.15, applied as a 0.025 wt % spray liquor, has a good fungicidal action (100%).

We claim:

1. An unsaturated cyclohexylacetic acid compound of the formula I:

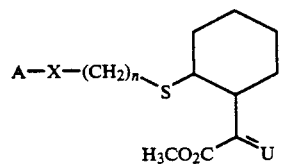

wherein
U is NOCH$_3$, CHOCH$_3$, CH$_2$, CH—CH$_3$, CH—CH$_2$—CH$_3$, N—NH—CH$_3$ or CH—S—CH$_3$,
n is from 0 to 10,
A is hydrogen; phenyl; phenyl substituted by from 1 to 3 identical or different substituents selected from the group consisting of halogen, C$_1$-C$_8$-alkyl, C$_1$-C$_8$-alkylthio, C$_1$-C$_8$-alkylsulfinyl, cyano, hydroxyl, nitro, C$_1$-C$_8$-alkoximino, C$_1$-C$_8$-alkoxy, phenyl, C$_1$-C$_4$-haloalkyl, C$_1$-C$_8$-alkenyloximino, formyl and C$_1$-C$_9$-alkylcarbonyl; heteroaryl; alkyl; substituted heteroaryl or substituted alkyl, wherein the substituents on the heteroaryl and alkyl groups are from 1 to 3 identical or different substituents selected from the group consisting of halogen, C$_1$-C$_8$-alkyl, C$_1$-C$_8$-alkylthio, C$_1$-C$_8$-alkyl-sulfinyl, cyano, hydroxyl, nitro, C$_1$-C$_8$-alkoximino, C$_1$-C$_8$-alkoxy, phenyl, C$_1$-C$_4$-haloalkyl, C$_1$-C$_8$-alkyenyloximino, formyl, C$_1$-C$_9$-alkylcarbonyl, C$_1$-C$_8$-alkoxycarbonyl, and phenyl which is substituted by from 1 to 3 identical or different substituents selected from the group consisting of halogen, C$_1$-C$_8$-alkyl, C$_1$-C$_8$-alkylthio, C$_1$-C$_8$-alkylsulfinyl, cyano, hydroxyl, nitro, C$_1$-C$_8$-alkoximino, C$_1$-C$_8$-alkoxy, phenyl, C$_1$-C$_4$-haloalkyl, C$_1$-C$_8$-alkenyloximino, formyl and C$_1$-C$_9$-alkylcarbonyl,
X is a single bond when n is 0, and oxygen, sulfur or a single bond when n is not 0,
and a plant-compatible acid base salt thereof.

2. The compound of the formula I as set forth in claim 1, where
U is =NOCH$_3$,
n is 1,
A is phenyl, and
X is a single bond.

3. A fungicide containing an inert carrier and a fungicidally effective amount of a compound of the formula I:

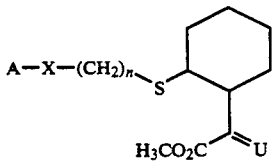

wherein

U is $NOCH_3$, $CHOCH_3$, $CH_2$, $CH-CH_3$, $CH-CH_2-CH_3$, $N-NH-CH_3$ or $CH-S-CH_3$, n is from 0 to 10, A is hydrogen; phenyl; phenyl substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl; heteroaryl; alkyl; substituted heteroaryl or substituted alkyl, wherein the substituents on the heteroaryl and alkyl groups are from 1 to 3 identical or different substituents selected from the group consisting of halogen, $C_1-C_8$-alkyl, $C_1-C_8$-alkylthio, $C_1-C_8$-alkyl-sulfinyl, cyano, hydroxyl, nitro, $C_1-C_8$-alkoximino, $C_1-C_8$-alkoxy, phenyl, $C_1-C_4$-haloalkyl, $C_1-C_8$-alkyenyloximino, formyl, $C_1-C_9$-alkylcarbonyl, $C_1-C_8$-alkoxycarbonyl, and phenyl which is substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl, X is a single bond when n is 0, and oxygen, sulfur or a single bond when n is not 0, and a plant-compatible acid base salt thereof.

4. An insecticide containing an inert carrier and an insecticidally effective amount of a compound of the formula I:

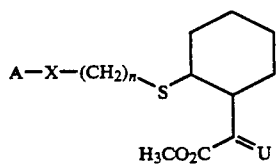

wherein

U is $NOCH_3$, $CHOCH_3$, $CH_2$, $CH-CH_3$, $CH-CH_2-CH_3$, $N-NH-CH_3$ or $CH-S-CH_3$, n is from 0 to 10, A is hydrogen; phenyl; phenyl substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl; heteroaryl; alkyl; substituted heteroaryl or substituted alkyl, wherein the substituents on the heteroaryl and alkyl groups are from 1 to 3 identical or different substituents selected from the group consisting of halogen, $C_1-C_8$-alkyl, $C_1-C_8$-alkylthio, $C_1-C_8$-alkyl-sulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl, $C_1-C_9$-alkylcarbonyl, $C_1-C_8$-alkoxycarbonyl, and phenyl which is substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl, X is a single bond when n is 0, and oxygen, sulfur or a single bond when n is not 0, and a plant-compatible acid base salt thereof.

5. A process for combating fungi, wherein the fungi or the plants, seed, materials or the soil to be protected against fungus attack are treated with a fungicidally effective amount of a compound of the formula I:

wherein

U is $NOCH_3$, $CHOCH_3$, $CH_2$, $CH-CH_3$, $CH-CH_2-CH_3$, $N-NH-CH_3$ or $CH-S-CH_3$, n is from 0 to 10, A is hydrogen; phenyl; phenyl substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl; heteroaryl; alkyl; substituted heteroaryl or substituted alkyl, wherein the substituents on the heteroaryl and alkyl groups are from 1 to 3 identical or different substituents selected from the group consisting of halogen, $C_1-C_8$-alkyl, $C_1-C_8$-alkylthio, $C_1-C_8$-alkyl-sulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl, $C_1-C_9$-alkylcarbonyl, $C_1-C_8$-alkoxycarbonyl, and phenyl which is substituted by from 1 to 3 identical or different substituents selected from the group consisting of halogen, $C_1-C_8$-alkyl, $C_1-C_8$-alkylthio, $C_1-C_8$-alkylsulfinyl, cyano, hydroxyl, nitro, $C_1-C_8$-alkoximino, $C_1-C_8$-alkoxy, phenyl, $C_1-C_4$-haloalkyl, $C_1-C_8$-alkenyloximino, formyl and $C_1-C_9$-alkylcarbonyl, X is a single bond when n is 0, and oxygen, sulfur or a single bond when n is not 0, and a plant-compatible acid base salt thereof.

* * * * *